United States Patent [19]

Maillefer et al.

[11] Patent Number: 5,658,145

[45] Date of Patent: Aug. 19, 1997

[54] SET OF INSTRUMENTS FOR BORING DENTAL RADICULAR CANALS AND METHOD THEREFOR

[75] Inventors: Pierre-Luc Maillefer, Ballaigues; François Aeby, Montagny-Pres-Yverdon, both of Switzerland

[73] Assignee: Maillefer Instruments S.A., Switzerland

[21] Appl. No.: 629,316

[22] Filed: Apr. 8, 1996

[30] Foreign Application Priority Data

Dec. 20, 1995 [CH] Switzerland .................. 3603/95

[51] Int. Cl.⁶ .................................................. A61C 5/02
[52] U.S. Cl. ............................................................ 433/102
[58] Field of Search ............................ 433/102, 165, 433/224

[56] References Cited

U.S. PATENT DOCUMENTS

| | | | |
|---|---|---|---|
| 2,902,763 | 8/1959 | Heppe | 433/165 |
| 4,538,989 | 9/1985 | Apairo, Jr. et al. | 433/102 |
| 4,738,616 | 4/1988 | Reynaud | 433/165 |
| 4,971,556 | 11/1990 | Ritano | 433/102 |
| 5,219,284 | 6/1993 | Velvart et al. | 433/102 |
| 5,257,934 | 11/1993 | Cossellu | 433/102 |

FOREIGN PATENT DOCUMENTS 3620527  12/1987  Germany .................. 433/102

Primary Examiner—Nicholas D. Lucchesi
Attorney, Agent, or Firm—Silverman, Cass & Singer, Ltd.

[57] ABSTRACT

A set of instruments for boring dental radicular canals in which the conicity of the rear part of the set positioned beyond the diameter $D_9$ of the instruments, increases more for the first instruments of the set than for the last ones. The conicity of the front part of the instruments does not increase much for the first instruments of the set, but does increase for the last ones. Hence, while using successively the instruments of a set, the dentist bores first the coronary portion of the tooth, then its medium portion and then its apical portion. The end part of the instruments, between the point thereof and their diameter $D_3$, situated at 3 mm from the point, is provided with one or several grooves for elimination of the dental scraps, but which have no cutting edges so that this part of the instruments functions only for their guidance.

4 Claims, 1 Drawing Sheet

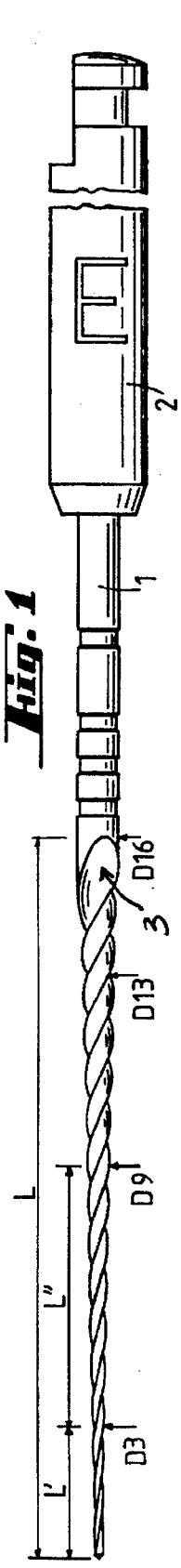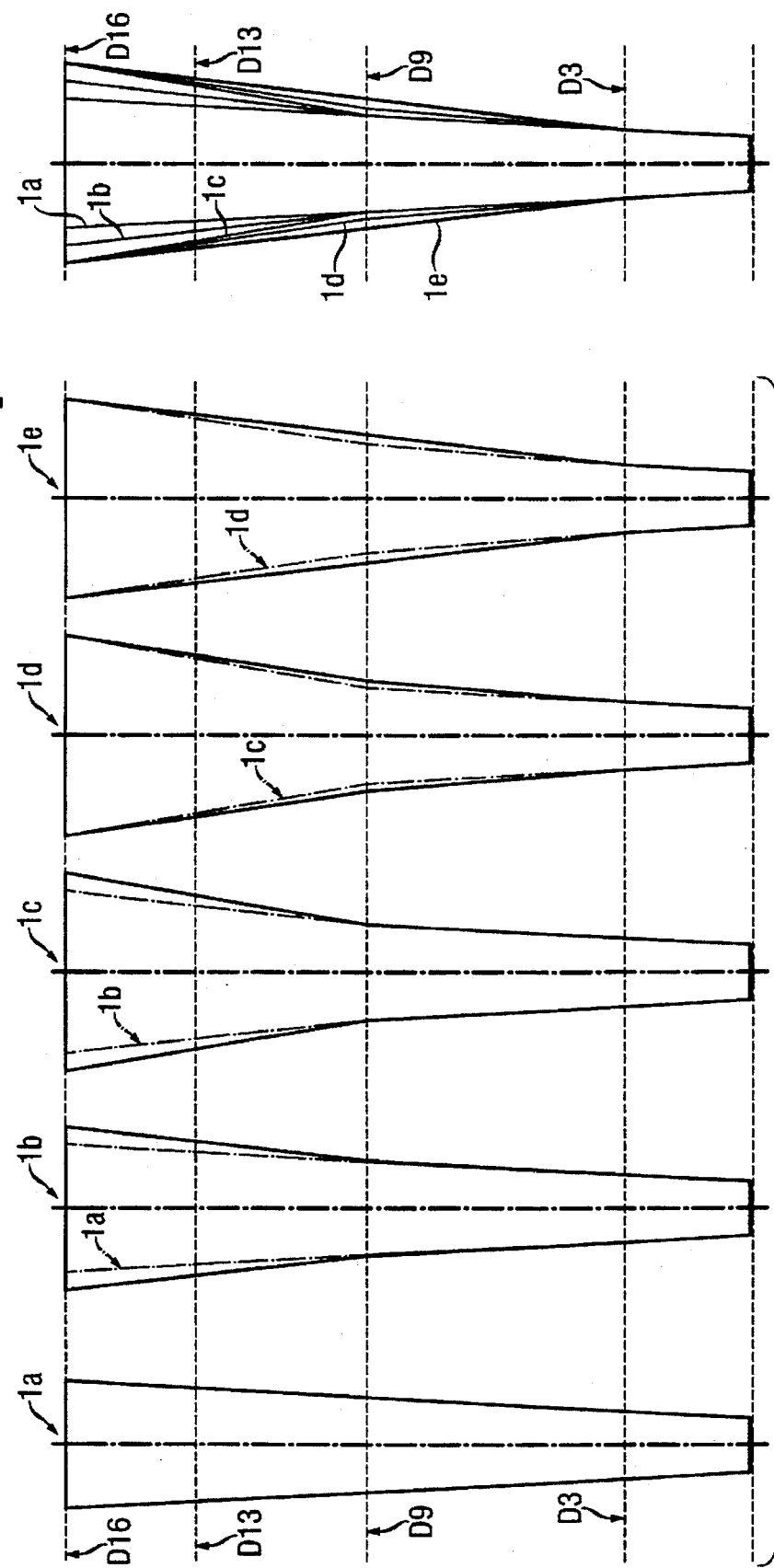

SET OF INSTRUMENTS FOR BORING DENTAL RADICULAR CANALS AND METHOD THEREFOR

BACKGROUND OF THE INVENTION

1. Field of the Invention

The present invention relates to a method for boring dental radicular canals by means of a set of instruments which are successively passed through the said canals.

The invention also relates to a set of instruments for carrying out the method in which each instrument comprises a tapered stem provided, on at least a part of its length which constitutes its active portion, at least one helicoidal cutting edge. This stem presents a conicity, the angle or opening of which is higher, at its rear end, than the angle at its front end.

2. Description of the Prior Art

The boring of dental radicular canals comprises a first step called catheterization, which consists in engaging into the radicular canal a very fine instrument, up to the apical foramen. This operation is always performed manually.

The widening of the radicular canal is effected by several operations which can be performed either manually or by means of instruments mechanically driven. For this second step, two methods can be used: The first one, called "step back" consists of introducing into the canal a succession of instruments, the diameters of which are successively increasing, while reducing the part of the length of the canal which is bored at each application of an instrument having increasing diameter. This method is relatively long and does not permit the dentist to observe, so far as it is possible, the work which has been effected. The second method, called "crown-down", consists of opening, in a first step, the coronary portion of the tooth, then to enter, by means of a set of instruments which successively increase in fineness up to the apical zone of the tooth.

The known sets of instruments permitting carrying out of these methods are usually mounted in a hand-piece rotating slowly (250 to 500 t/min.); they are formed, in most of the cases, of a nickel-titanium alloy, and belong to three families:

The first family comprises a set of instruments formed of a short cutting portion, followed by a thin and flexible collet which is itself connected to a handle which is secured to a hand-piece to enable mechanical driving of the instrument. The diameter of the active portion of the instrument increases according to an arithmetic progression, the interval between two numbers of the instruments of the set being of 0.025 mm.

A second family comprises instruments the active portion of which, of a length of 16 mm, has a conicity of 0.04 mm per millimeter of length. This active portion is immediately followed by a cylindrical portion to permit connection with the handle of the instrument. The progression of the diameter at the point of the end of the active portion of the instrument is of 29% between each number of the instruments of the set.

Finally, a last family comprises instruments having an active length of 16 mm and presenting a conical envelope, all of these instruments having the same diameter at their end. Their conicity increases 0.05 mm for each number of the instruments of the set.

SUMMARY OF THE INVENTION

The object of the present invention is to furnish on the one hand a new boring method for dental radicular canals, after the step of catheterism, and on the other hand new instruments permitting carrying out this method, which is safer and more efficient than the known methods. This new method is also more rapid and does not need as many instruments as the known methods.

Moreover, the instruments used for carrying out this method produce borings which are more regular, having a continuous wall, that is not always the case with the known instruments.

These purposes are achieved because, in the method of the present invention, one attacks first the coronary portion of the tooth by means of the first instrument of the set, then the medium portion of the tooth, by means of the next instruments of the set, and finally the apical portion of the tooth by means of the last instruments of the set.

The purposes are also reached due to the fact that, in the set of instruments of the invention, the conicity of the stem of the instruments increases, on the rear portion of the active length of the instruments, more for the first instruments of the set than for the last ones, while, on the contrary, on the front portion of their active part, it is the conicity of the last instruments of the set which increases more than the conicity of the first instruments of the set.

The various features of the invention will be apparent from the following description, drawings and claims, the scope of the invention not being limited to the drawings themselves as the drawings are only for the purpose of illustrating ways in which the principles of the invention can be applied. Other embodiments of the invention utilising the same or equivalent principles may be used and structural changes may be made as desired by those skilled in the art without departing from the present invention and the purview of the appended claims.

BRIEF DESCRIPTION OF THE DRAWINGS

FIG. 1 is an elevational view of an instrument for the boring of dental radicular canals.

FIG. 2 represents the profile of five instruments for the boring of dental radicular canals belonging to a set of such instruments, and FIG. 3 represents the superposed profile of the five instruments of FIG. 2.

In FIGS. 2 and 3 the diameter of the instruments has been exaggerated with respect to their length, so as to render more visible the variations of the conicity of the instruments.

DESCRIPTION OF THE PREFERRED EMBODIMENTS

The instrument represented in FIG. 1 comprises stem 1 of circular cross-section, made of a nickel-titanium alloy, engaged, at its rear part, in a handle 2 intended to be engaged in a hand-piece to enable mechanical driving of the instrument.

The stem 1 is tapered, its front part, indicated at L, being provided with two helicoidal grooves 3, having each a cutting edge. At the end of the instrument, along a length indicated by L', of about 3 mm, ending in a point indicated by $D_3$, expressing the diameter of the instrument at this point, the cutting edge of the helicoidal grooves 3 has been eliminated so that, along this length, the instrument does not cut and the grooves are provided only to eliminate the chips or scraps of the dental material removed by the instrument. The number of the cutting grooves can be greater than two.

From point $D_9$ of the instrument, situated at a distance L" from point $D_3$ of 6 mm, that is to say at a distance of 9 mm from the point of the instrument, the conicity of the instrument increases slightly as shown by the first instrument, indicated by reference 1a of FIG. 2.

The instrument retains this new conicity up to point $D_{16}$ which is situated at the end of its active portion L.

The second instrument of the set of FIG. 2, designated by reference 1b, is distinguished from the first one by the fact that the angle or opening of the conicity of its portion situated between the points $D_9$ and $D_{16}$ increases more than for the instrument 1a.

The same is true for the third instrument, designated by reference 1c, of the set of FIG. 2.

The difference of conicity of the rear part of the active length of the instruments, from their point $D_9$, appears clearly in FIG. 2, where the profile of the instrument 1a has been indicated in dot-and-dash lines on the instrument 1b, and the profile of the instrument 1b has been indicated on the instrument 1c.

FIG. 2 also shows that the conicity of the front part of the instruments 1a, 1b and 1c, between the end of these instruments and their diameter $D_9$, is the same for these three instruments.

So far as the fourth instrument of the set is concerned, designated by reference 1d, the conicity of its front part, before the diameter $D_9$, increases with respect to that of the instrument 1c. The conicity of its rear part increases also with respect to the instrument 1c, but to a lesser degree. This is the same for the fifth and last instrument of the set, designated by reference 1e, in which the conicity of its front and rear parts increases with respect to the instrument 1c.

The set of instruments of the invention permits the dentist who has manually executed the first step of the boring, called catheterism, consisting in engaging into the canal a very fine instrument, up to the apical formamen, to then use successively, the instruments 1a to 1e of the set, mechanically driven, while starting with instrument 1a and ending with instrument 1e.

This successive use of the several instruments of the set permits a progressive working, to be effected each instrument broadening or widening a specific portion of the radicular canal while being guided, up to the apex, by its ending front part which does not cut. This also permits the dentist to avoid deviations and offsets with respect to the natural curve of the initial canal.

It is coronary portion of the canal which is bored the first, that produces a maximum output of dental scraps and optimal conditions of work for the next instrument. Incidentally, in this manner, the risk of producing an infection by the introduction of decayed dental tissue to the apex is highly reduced. The median portion of the tooth is bored next, and its apical portion is bored last.

The end of the apical portion is not needlessly bored due to the fact that the end part of the instrument, the conicity of which will be of 2% for example, on a length of 3 mm, has no cutting edges.

The present method of boring and the set of instruments for carrying out the method enable realization of a canal which is more bell-mouthed and especially more regular, that results in conditions of obturation of the canal which are optimum. The passage of the last instrument 1e results in finishing boring.

The radicular canal which is bored as here-above mentioned has no solution of continuity along its surface, forming stairs as is the case when known instruments, especially instruments of the so-called type of Gates, are used.

In the example as disclosed and represented, the conicity of the instruments of the set varies only in one point, at the level of the diameter $D_9$. One could however provide the case where the conicity will vary in more than one point, for instance at the level of the diameter $D_9$ and of the diameter $D_{13}$ situated at 13 mm from the point of the instrument.

In the same manner, the open-trumpet-shape of the instrument could be achieved by a continuous variation of the angle of its cone. In this case, the generating line of its surface will not be constituted by a broken line, as in the case of the example which has been disclosed and represented, but by a curve urging towards the central axis of the instrument, beyond the end thereof.

Preferably, the conicity of the front part of the instrument, positioned forward of the diameter $D_9$ thereof, will be of the order of 2%, the conicity of the rear part being variable from 4.5% to almost 6%.

The number of the instruments of the set could be greater or less than five, which is the case of the example as disclosed and represented.

We claim:

1. Set of instruments for boring dental radicular canals comprising, each instrument having a tapered stem, said stem including at least one helicoidal cutting edge on at least a part of its length which forms the active portion of the stem, the stem having a conicity the angle of opening of which is greater at its rear end than the angle at its front end, the conicity of the stem of the instruments increasing on the rear portion of the active length of the instruments at a greater rate for the first instruments of the set than for the last ones, the conicity of the stem of the instruments increasing on the front portion of the active length of the instruments at a greater rate for the last instruments of the set than for the first ones.

2. Set of instruments as claimed in claim 1, in which the active portion of each instrument of the set includes at least two portions of different conicity, the angle of opening of said last named two portions increasing from the front end of the said active portion in the direction of its rear end.

3. Set of instruments as claimed in claims 1, in which each instrument of the set includes a revolution body the generating line of which is a curve the tangential line of which at any point forms, with the longitudinal axis of the instrument, an angle which increases from the front end of the active portion of the instrument in the direction of its rear end.

4. Set of instruments as claimed in claim 1, in which the front end of each instrument is not provided with cutting edges but is provided with at least a helicoidal groove, said helicoidal grove having a non cutting edge to eliminate the scraps of the dental material removed by the instrument during working thereof.

* * * * *

UNITED STATES PATENT AND TRADEMARK OFFICE
CERTIFICATE OF CORRECTION

PATENT NO. : 5,658,145
DATED : August 19, 1997
INVENTOR(S) : Pierre-Luc Maillefer and Francois Aeby It is certified that error appears in the above-indentified patent and that said Letters Patent is hereby corrected as shown below:

Column 4, line 48, change "claims" to --claim--.

Signed and Sealed this

Twenty-fifth Day of November, 1997

*Attest:*

BRUCE LEHMAN

*Attesting Officer*　　　　*Commissioner of Patents and Trademarks*